United States Patent [19]  
Dodds et al.

[11] 4,299,989  
[45] Nov. 10, 1981

[54] PREPARATION OF KETONES

[75] Inventors: Alan R. Dodds, Elgin; Tamotsu Imai, Mt. Prospect, both of Ill.

[73] Assignee: UOP Inc., Des Plaines, Ill.

[21] Appl. No.: 145,952

[22] Filed: May 2, 1980

[51] Int. Cl.³ ............................................. C07C 45/41
[52] U.S. Cl. .................................................... 568/397
[58] Field of Search ............................... 568/397, 319
[56] References Cited

U.S. PATENT DOCUMENTS

| | | | |
|---|---|---|---|
| 2,395,012 | 2/1946 | Reeder et al. | 568/397 |
| 2,530,512 | 11/1950 | Drewitt | 568/397 |
| 2,686,204 | 8/1954 | Watson et al. | 568/397 |
| 3,257,459 | 6/1966 | Swakon et al. | 568/311 |
| 3,468,956 | 9/1969 | Mead | 568/397 |
| 3,792,066 | 2/1974 | Rothman et al. | 568/397 |
| 3,857,893 | 12/1974 | Nozaki | 568/387 |
| 3,884,981 | 5/1975 | Kiff | 568/397 |
| 4,034,047 | 7/1977 | Angstadt | 568/836 |

OTHER PUBLICATIONS

Yakenson et al., Chem. Abst., vol. 56, #3340i.

Primary Examiner—Natalie Trousoe  
Assistant Examiner—James H. Reamer  
Attorney, Agent, or Firm—James R. Hoatson, Jr.; Raymond H. Nelson; William H. Page, II

[57] ABSTRACT

Ketones may be prepared from carboxylic acid esters by treating said esters at elevated temperatures in the range of from about 50° to about 300° C. and pressures ranging from 1 to about 300 atmospheres in the presence of a catalyst comprising a compound containing a metal of Group VIII of the Periodic Table. In addition, reaction is also effected in the presence of a quaternary alkylammonium salt which will increase the conversion of the ester to the desired ketone. Examples of catalysts which are employed will include the salts, carbonyls, and organometallic complexes of rhodium and cobalt.

5 Claims, No Drawings

PREPARATION OF KETONES

SUMMARY OF THE INVENTION

This invention relates to a process for the preparation of ketones. More specifically, the invention is concerned with a process for preparing ketones utilizing carboxylic acid esters as the starting materials.

Ketonic compounds find a wide variety of uses in the chemical field. For example, one of the most common ketones, namely acetone, is used in the synthesis of acidic anhydride or derivatives such as diacetone alcohol, mesityl oxide, etc. In addition, it is also used as a solvent for cellulose acetate, in paints, lacquers and adhesives, epoxy resins, fibers, pharmaceuticals, rubber antioxidants, etc. Likewise, methyl ethyl ketone is used in lacquers, paint removers, cement and adhesives, celluloid, in the dewaxing of lubricating oil, in the manufacture of smokeless powder, as a solvent, cleaning fluid, printing, as well as artificial leather dressings and dyes.

It is therefore an object of this invention to provide a process for producing ketones.

A further object of this invention is to provide a process for producing ketones utilizing carboxylic acid ester as a starting material.

In one aspect an embodiment of this invention resides in a process for the production of a ketone which comprises treating a carboxylic acid ester in the presence of a catalyst comprising a compound containing a metal of Group VIII of the Periodic Table at treating conditions, and recovering the resultant ketone.

A specific embodiment of this invention is found in a process for the production of a ketone which comprises treating methyl formate in the presence of a catalyst comprising chlororhodium phthalocyanine at a temperature in the range of from 50° to about 300° C. and a pressure in the range of from about 1 to about 300 atmospheres, said pressure being afforded by the presence of carbon monoxide, and in the added presence of dichlorobenzylalkyldimethylammonium chloride, and recovering the resultant acetone.

Other objects and embodiments will be found in the following further detailed description of the present invention.

As hereinbefore set forth, the present invention is concerned with a process for producing ketones in which the starting material comprises a carboxylic acid ester. The process is effected by treating the ester at an elevated temperature and pressure, in which the pressure is afforded by the presence of carbon monoxide or a mixture of carbon monoxide and hydrogen in the presence of a catalyst comprising a compound containing a metal of Group VIII of the Periodic Table. In addition, it has also been discovered that when the reaction is effected in the added presence of a quaternary alkylammonium salt the conversion of the ester will be significantly increased with only a relatively light drop in selectivity to the desired ketone.

Examples of carboxylic acid esters which may be employed will include such esters in which the alkyl portion of the ester will contain from 1 to about 6 carbon atoms or more while the carboxylic acid portion of the ester will also contain from 1 to about 6 carbon atoms or more, preferably formic acid. Specific examples of these esters which may be employed as starting materials will include methyl formate, ethyl formate, propyl formate, n-butyl formate, t-butyl formate, n-pentyl formate, secpentyl formate, n-hexyl formate, sec-hexyl formate, methyl acetate, ethyl acetate, propyl acetate, n-butyl acetate, t-butyl acetate, n-pentyl acetate, sec-pentyl acetate, n-hexyl acetate, sec-hexyl acetate, methyl propionate, ethyl propionate, propyl propionate, n-butyl propionate, t-butyl propionate, n-pentyl propionate, sec-pentyl propionate, n-hexyl propionate, sechexyl propionate, methyl butyrate, ethyl butyrate, propyl butyrate, n-butyl butyrate, t-butyl butyrate, n-pentyl butyrate, sec-pentyl butyrate, n-hexyl butyrate, sec-hexyl butyrate, methyl valerate, ethyl valerate, propyl valerate, n-butyl valerate, t-butyl valerate, n-pentyl valerate, sec-pentyl valerate, n-hexyl valerate, sec-hexyl valerate, methyl caproate, ethyl caproate, propyl caproate, n-butyl caproate, t-butyl caproate, n-pentyl caproate, sec-pentyl caproate, n-hexyl caproate, sec-hexyl caproate, etc. It is also contemplated within the scope of this invention that aryl esters of carboxylic acids such as phenyl formate, phenyl acetate, phenyl propionate, benzyl formate, benzyl acetate, benzyl propionate, o-tolyl formate, m-tolyl formate, p-tolyl formate, o-tolyl acetate, m-tolyl acetate, p-tolyl acetate, etc., may also be employed although not necessarily with equivalent results.

Examples of catalysts comprising a compound containing a metal of Group VIII of the Periodic Table and particularly rhodium and cobalt containing compounds which may be employed will include salts, carbonyls and organometallic complexes of metals. Some specific examples which may be employed will include rhodium chloride, rhodium bromide, rhodium iodide, rhodium nitrate, chlorodicarbonylrhodium dimer, rhodium carbonyl, chlorobis(ethylene)rhodium dimer, hexarhodiumhexadecacarbonyl, tetrarhodiumdodecacarbonyl, rhodium acetate, rhodium acetylacetonate, chlororhodium phthalocyanine, chlororhodium phthalocyanine monosulfonate, chlororhodium phthalocyanine disulfonate, chlororhodium phthalocyanine tetrasulfonate, chlorocarbonylbis(trisphenylphosphine)rhodium (I), nitrosyltris(triphenylphosphine)rhodium, hydridocarbonyltris(triphenylphosphine)rhodium (I), cobalt chloride, cobalt bromide, cobalt iodide, cobalt nitrate, cobalt carbonyl, cobalt phthalocyanine, cobalt phthalocyanine monosulfonate, cobalt phthalocyanine disulfonate, cobalt phthalocyanine tetrasulfonate, triphenylphosphinecobalttricarbonyl dimer, cyclopentadienenylcobaltdicarbonyl, bis(triphenylphosphine)iminium tetracarbonylcobaltate, cobalticinium hexafluorophosphate, etc. It is to be understood that the aforementioned compounds which are employed as catalysts in the process of this invention are only representative of the catalyst which may be employed and that the present process is not necessarily limited thereto.

In addition to employing a catalyst of the type hereinbefore set forth, it is also contemplated within the scope of this invention that the conversion of the aforementioned esters may be increased by the presence of a quaternary alkylammonium salt in the reaction mixture. Examples of these salts which may be present will include trimethylphenylammonium chloride, triethylphenylammonium chloride, tripropylphenylammonium chloride, tributylphenylammonium chloride, trimethylbenzylammonium chloride, triethylbenzylammonium chloride, tripropylbenzylammonium chloride, tetramethylammonium chloride, tetraethylammonium chloride, tetrapropylammonium chloride, tetrabutylammonium chloride, trimethylethylammonium chloride, trimethylpropylammonium chloride, trimethylbutylammonium chloride, triethylpropylammonium chloride, triethylbutylammonium chloride, dichlorobenzylalkyldimethylammonium chloride, dichlorobenzylalkyldimethylammonium bromide, dichlorobenzylalkyldimethylammonium iodide, etc. The reaction conditions which are employed to produce the desired ketones from the carboxylic acid esters will include elevated temperatures in the range of from about 50° to about 300° C. and pressures ranging from about 1 to about 300 atmospheres. The elevated pressures which are employed will be afforded by the presence of either carbon monoxide or a mixture of carbon monoxide and hydrogen in which the ratio of carbon monoxide to hydrogen will range from about 20% carbon monoxide to about 100% carbon monoxide, the preferred ratio being about 50:50 parts of carbon monoxide and hydrogen.

The process of this invention may be effected in any suitable manner and may comprise a batch or continuous type operation. For example, when a batch type of operation is employed a quantity of the carboxylic acid ester of the type hereinbefore set forth in greater detail is placed in an appropriate pressure resistant vessel such as an autoclave of the rotating, mixing or stirring type, etc., along with the catalyst comprising a compound containing a metal of Group VIII of the Periodic Table. In addition, if so desired, the promoter comprising a quaternary alkylammonium compound is also placed in the vessel which is thereafter sealed. The pressure forming gas such as carbon monoxide or a combination of carbon monoxide and hydrogen is charged thereto until the desired operating pressure has been attained. Thereafter the vessel and contents thereof are heated to the desired operating temperature and maintained thereat for a predetermined period of time which may range from about 0.5 up to about 10 hours or more in duration. Upon completion of the desired operating time, heating is discontinued and after the vessel has returned to room temperature the excess pressure is discharged. The reaction mixture is recovered from the vessel and subjected to conventional means of separation such as filtration, distillation, etc., whereby the desired ketone is separated from any unreacted starting material, catalyst, promoter, etc., and recovered.

In addition to the batch type operation, it is also contemplated within the scope of this invention that a continuous manner of operation may also be employed. When utilizing this type of operation, a quantity of the carboxylic acid ester is continuously charged to a reaction zone which is maintained at the proper operating conditions of temperature and pressure and which will contain a catalyst of the type previously discussed as well as a promoter. After passage through the zone for a predetermined period of time, the reactor effluent is continuously withdrawn and subjected to conventional means of separation whereby the desired ketone may be separated and recovered while any unreacted carboxylic acid ester, catalyst, and promoter may be recycled to the reaction zone to form a portion of the feed stock.

Examples of ketones which may be produced according to the process of this invention will include symmetrical ketones such as acetone, diethyl ketone, di-n-propyl ketone, diisopropyl ketone, di-n-butyl ketone, di-t-butyl ketone, di-n-pentyl ketone, etc., as well as unsymmetrical ketones such as methyl ethyl ketone, methyl propyl ketone, methyl butyl ketone, methyl pentyl ketone, ethyl propyl ketone, ethyl butyl ketone, ethyl pentyl ketone, propyl butyl ketone, propyl pentyl ketone, etc.

The following examples are given for purposes of illustrating the process of this invention. However, it is to be understood that these examples are given merely for purposes of illustration and that the present invention is not necessarily limited thereto.

EXAMPLE I

In this example 0.62 gram of a catalyst comprising chlororhodium phthalocyanine along with 15.4 cc of methyl formate and 5.0 cc of a quaternary alkylammonium salt comprising a 50% aqueous solution of dichlorobenzylalkyldimethylammonium chloride in which 61% of the alkyl groups are n-dodecane, said compound being sold under the tradename Maquat DLC 1214 by the Mason Chemical Company. The autoclave was sealed and 50 atmospheres of carbon monoxide was charged to the reactor at room temperature. The autoclave was then heated to a temperature of 100° C. and maintained thereat for a period of 4 hours, the maximum pressure during this time reaching 70 atmospheres. At the end of the 4 hour period heating was discontinued and after the reactor had returned to room temperature the excess pressure was discharged. The autoclave was opened and the reaction mixture was recovered therefrom. Analysis of this mixture by means of gas chromatography disclosed that there had been a 61.1% conversion of the methyl formate to acetone at a 61.4% selectivity.

EXAMPLE II

The above experiment was repeated by placing 0.62 gram of chlororhodium phthalocyanine in an autoclave along with 15.4 cc of methyl formate. However, this experiment was performed in the absence of a quaternary alkylammonium salt but in the presence of 0.9 cc of iodobenzene. After sealing the autoclave, 48 atmospheres of carbon monoxide was charged to the autoclave which was then heated to a temperature of 150° C. The autoclave was maintained at this temperature for a period of 4 hours, the maximum pressure during this time reaching 79 atmospheres. At the end of the 4 hour period heating was discontinued and the autoclave was allowed to return to room temperature. The excess pressure was discharged, the autoclave was opened and the reaction mixture recovered therefrom. Analysis of this mixture by means of gas chromatography disclosed that there had been only a 17.9% conversion of the methyl formate to acetone at a 72.8% selectivity.

EXAMPLE III

A repeat of the above experiments treating other carboxylic acid esters such as a mixture of methyl formate and ethyl formate or ethyl acetate in the presence of other catalysts such as rhodium carbonyl or chlorodicarbonylrhodium dimer using various quaternary alkylammonium salts such as trimethylphenylammonium chloride or triethylpropylammonium chloride may also disclose that a greater conversion of the esters to methyl ethyl ketone or diethyl ketone may result than when the conversion if effected in the absence of the aforesaid quaternary alkylammonium salts.

We claim as our invention:
1. A process for the production of a ketone which comprises treating an alkyl carboxylic acid ester, wherein said carboxylic acid portion of said ester is selected from the group consisting essentially of formate, acetate, propionate, butyrate, valerate and caproate and wherein the alkyl portion of said ester is selected from the group consisting essentially of a methyl-, ethyl-, propyl-, n-butyl-, t-butyl-, n-pentyl-, sec-pentyl-, n-hexyl- and sec-hexyl- moiety in the presence of (1.) an atmosphere consisting essentially of carbon monoxide, (2.) a quaternary alkylammonium salt selected from the group consisting essentially of trimethylphenyl-, triethylphenyl-, tripropylphenyl-, tributylphenyl-, trimethylbenzyl-, triethylbenzyl-, tripropylbenzyl-, tetramethyl-, tetraethyl-, tetrapropyl-, tetrabutyl-, trimethylethyl-, trimethylpropyl-, trimethylbutyl-, triethylpropyl-, and triethylbutyl- ammonium chloride, dichlorobenzylalkyldimethylammonium chloride, dichlorobenzylalkyldimethylammonium bromide and dichlorobenzylalkyldimethylammonium iodide and (3.) a catalyst consisting essentially of a salt, carbonyl or organometallic complex of rhodium or cobalt selected from the group consisting essentially of rhodium or cobalt chloride, bromide, iodide, nitrate, or carbonyl, chlorodicarbonylrhodium dimer, chloro-bis (ethylene) rhodium dimer, hexarhodiumhexadecacarbonyl, tetrarhodium dodecarbonyl, rhodium acetate, rhodium acetylacetonate, chlororhodium or cobalt phthalocyanine, chlororhodium or cobalt phthalocyanine mono-, di- or tetrasulfonate, chlorocarbonyl- bis(triphenylphosphine)rhodium (I), nitrosyltris(triphenylphosphine)rhodium, hydridocarbonyltris(triphenylphosphine)rhodium (I), triphenylphosphinecobalttricarbonyl dimer, cyclopentadienenylcobaltdicarbonyl, bis(triphenylphosphine)iminium tetracarbonylcobaltate and cobaltiminium hexafluorophosphate at a temperature of from about 50° to about 300° C. and a pressure in the range of from about 1 to about 300 atmospheres, and recovering said resultant ketone.

2. The process as set forth in claim 1 in which said atmosphere comprises a mixture of carbon monoxide and hydrogen.

3. The process as set forth in claim 1 in which said carboxylic acid ester is methyl formate and said ketone is acetone.

4. The process as set forth in claim 1 in which said carboxylic acid ester is a mixture of methyl formate and ethyl formate and said ketone is methyl ethyl ketone.

5. The process as set forth in claim 1 in which said carboxylic acid ester is ethyl acetate and said ketone is diethyl ketone.

* * * * *